(12) United States Patent
Falkovich

(10) Patent No.: US 11,878,140 B2
(45) Date of Patent: Jan. 23, 2024

(54) STERILIZATION ARRANGEMENT FOR DRUG DELIVERY DEVICE

(71) Applicant: Becton, Dickinson and Company, Franklin Lakes, NJ (US)

(72) Inventor: Margarita Falkovich, Paramus, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 18/115,369

(22) Filed: Feb. 28, 2023

(65) Prior Publication Data

US 2023/0201448 A1 Jun. 29, 2023

Related U.S. Application Data

(63) Continuation of application No. 17/153,613, filed on Jan. 20, 2021, which is a continuation of application
(Continued)

(51) Int. Cl.
*A61M 5/142* (2006.01)
*A61M 5/00* (2006.01)
(Continued)

(52) U.S. Cl.
CPC ........... *A61M 5/001* (2013.01); *A61L 2/0047* (2013.01); *A61L 2/10* (2013.01); *A61M 5/14248* (2013.01); *A61M 5/162* (2013.01); *A61L 2202/14* (2013.01); *A61L 2202/182* (2013.01); *A61L 2202/21* (2013.01); *A61M 5/14566* (2013.01); *A61M 5/20* (2013.01); *A61M 2005/14252* (2013.01); *A61M 2005/247* (2013.01);
(Continued)

(58) Field of Classification Search
CPC ............................................. A61M 2039/0285
See application file for complete search history.

(56) References Cited

U.S. PATENT DOCUMENTS 5,360,410 A 11/1994 Wacks
7,637,891 B2 12/2009 Wall
(Continued)

FOREIGN PATENT DOCUMENTS

CN 105999482 A 10/2016
EP 3348284 A2 7/2018
(Continued)

*Primary Examiner* — Jenna Zhang
(74) *Attorney, Agent, or Firm* — The Webb Law Firm

(57) ABSTRACT

A drug delivery system for injecting a medicament includes a housing defining a cavity, a container received within the cavity and configured to receive a medicament, the container comprising a stopper configured to move within the container and a closure, a drive assembly received within the cavity and configured to drive the stopper within the container, a needle actuator assembly received within the cavity and comprising a needle configured to be placed in fluid communication with the container, the needle moveable from a first position and a second position spaced from the first position, and a sterilizer received within the cavity and configured to sterilize at least one of the container, the drive assembly, and the needle actuator assembly upon activation of the drug delivery system.

17 Claims, 9 Drawing Sheets

Related U.S. Application Data

No. 16/160,114, filed on Oct. 15, 2018, now Pat. No. 10,926,023.

(60) Provisional application No. 62/572,715, filed on Oct. 16, 2017.

(51) Int. Cl.

| | |
|---|---|
| *A61M 5/162* | (2006.01) |
| *A61L 2/00* | (2006.01) |
| *A61L 2/10* | (2006.01) |
| *A61M 5/20* | (2006.01) |
| *A61M 5/145* | (2006.01) |
| *A61M 5/24* | (2006.01) |

(52) U.S. Cl.
 CPC ............... *A61M 2205/053* (2013.01); *A61M 2205/3317* (2013.01); *A61M 2205/585* (2013.01); *A61M 2205/8206* (2013.01); *A61M 2209/10* (2013.01)

(56) References Cited

U.S. PATENT DOCUMENTS

| | | | |
|---|---|---|---|
| 7,834,328 | B2 | 11/2010 | Redmond et al. |
| 7,857,131 | B2 | 12/2010 | Vedrine |
| 9,211,376 | B2 | 12/2015 | Kouyoumijan et al. |
| 10,245,424 | B2 | 4/2019 | Cohen et al. |
| 2005/0047975 | A1 | 3/2005 | Tang et al. |
| 2011/0125013 | A1 | 5/2011 | Neer |
| 2012/0068088 | A1 | 3/2012 | Durkin |
| 2013/0066274 | A1 | 3/2013 | O'Connor et al. |
| 2013/0303996 | A1 | 11/2013 | Rasooly et al. |
| 2013/0317422 | A1 | 11/2013 | Levenson et al. |
| 2013/0323120 | A1 | 12/2013 | Ma |
| 2015/0080800 | A1 | 3/2015 | Cronenberg |
| 2015/0352297 | A1 | 12/2015 | Stedman et al. |
| 2015/0352301 | A1 | 12/2015 | Stedman et al. |
| 2016/0045633 | A1 | 2/2016 | Pagan et al. |
| 2016/0058941 | A1 | 3/2016 | Wu et al. |
| 2016/0367767 | A1 | 12/2016 | Cashman et al. |
| 2017/0028132 | A1 | 2/2017 | Cronenberg et al. |
| 2017/0232185 | A1 | 8/2017 | Wilson et al. |
| 2017/0290977 | A1 * | 10/2017 | Schauderna .......... A61L 2/0082 |
| 2019/0022306 | A1 | 1/2019 | Gibson et al. |

FOREIGN PATENT DOCUMENTS

| | | |
|---|---|---|
| JP | 2017500996 A | 1/2017 |
| WO | 9302720 A1 | 2/1993 |
| WO | 2004024211 A2 | 3/2004 |
| WO | 2005018705 A2 | 3/2005 |
| WO | 2010133698 A2 | 11/2010 |
| WO | 2013155153 A1 | 10/2013 |
| WO | 2014179774 A1 | 11/2014 |
| WO | 2015081337 A2 | 6/2015 |
| WO | 2015191478 A1 | 12/2015 |
| WO | 2017093803 A1 | 6/2017 |
| WO | 2017142808 A1 | 8/2017 |

* cited by examiner

STERILIZATION ARRANGEMENT FOR DRUG DELIVERY DEVICE

CROSS-REFERENCE TO RELATED APPLICATION

The present application is a continuation of U.S. application Ser. No. 17/153,613, filed Jan. 20, 2021, which is a continuation application of U.S. application Ser. No. 16/160,114, filed Oct. 15, 2018, entitled "Sterilization Arrangement for Drug Delivery Device" (now U.S. Pat. No. 10,926,023), which claims priority to United States Provisional Application Ser. No. 62/572,715, filed Oct. 16, 2017, entitled "Sterilization Arrangement for Drug Delivery Device", the entire disclosures of each of which are hereby incorporated by reference.

BACKGROUND OF THE INVENTION

Field of the Invention

The present disclosure relates generally to a drug delivery device and, in particular, to a sterilization arrangement for a drug delivery device.

Description of Related Art

Various types of automatic injection or drug delivery devices have been developed to allow drug solutions and other liquid therapeutic preparations to be administered by untrained personnel or to be self-injected. Generally, these devices include a reservoir that is pre-filled with the liquid therapeutic preparation, and some type of automatic needle-injection mechanism that can be triggered by the user. When the volume of fluid or drug to be administered is generally below a certain volume, such as 1 mL, an auto-injector is typically used, which typically has an injection time of about 10 to 15 seconds. When the volume of fluid or drug to be administered is above 1 mL, the injection time generally becomes longer resulting in difficulties for the patient to maintain contact between the device and the target area of the patient's skin. Further, as the volume of drug to be administered becomes larger, increasing the time period for injection becomes desirable. The traditional method for a drug to be injected slowly into a patient is to initiate an IV and inject the drug into the patient's body slowly. Such a procedure is typically performed in a hospital or outpatient setting.

Certain devices allow for self-injection in a home setting and are capable of gradually injecting a liquid therapeutic preparation into the skin of a patient. In some cases, these devices are small enough (both in height and in overall size) to allow them to be "worn" by a patient while the liquid therapeutic preparation is being infused into the patient. These devices typically include a pump or other type of discharge mechanism to force the liquid therapeutic preparation to flow out of a reservoir and into the injection needle. Such devices also typically include a valve or flow control mechanism to cause the liquid therapeutic preparation to begin to flow at the proper time and a triggering mechanism to initiate the injection.

SUMMARY OF THE INVENTION

In one aspect, a drug delivery system for injecting a medicament includes a housing defining a cavity, a container received within the cavity and configured to receive a medicament, the container comprising a stopper configured to move within the container and a closure, a drive assembly received within the cavity and configured to drive the stopper within the container, a needle actuator assembly received within the cavity and comprising a needle configured to be placed in fluid communication with the container, the needle moveable from a first position and a second position spaced from the first position, and a sterilization arrangement received within the cavity and configured to sterilize at least one of the container, the drive assembly, and the needle actuator assembly upon activation of the drug delivery system.

In another aspect, the sterilization arrangement may include at least one light source that radiates ultraviolet light to sterilize at least one of the container, the drive assembly, and the needle actuator assembly. The at least one light source may include at least one light emitting diode (LED) light. The sterilization arrangement may include a power source operatively connected to the at least one light source. The power source may include at least one battery. The sterilization arrangement may include a sensor operatively connected to the power source and configured to send a signal to the power source upon initiation of a drug delivery process for the drug delivery system. An actuation button may be provided in the housing and movable between a first, inactive position and a second, activation position in which a drug delivery process of the drug delivery system is initiated. The actuation button may include a magnet that activates the sensor when the actuation button is moved from the first, inactive position to the second, activation position. The sensor may be a Hall Effect transistor sensor. The sterilization arrangement may include a timer operatively connected to the light source and configured to shut off the light source after a predetermined amount of time. The at least one light source may include four light sources. The light sources may be positioned on different inner side surfaces of the housing.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

DETAILED DESCRIPTION

Figure 1:
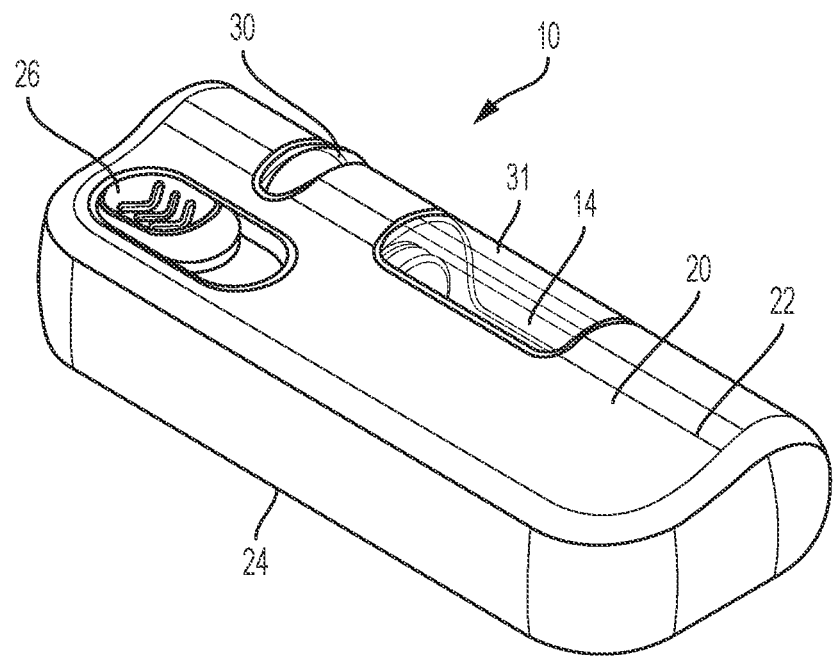
FIG. 1 is a perspective view of a drug delivery system according to one aspect of the present invention.
Figure 2:
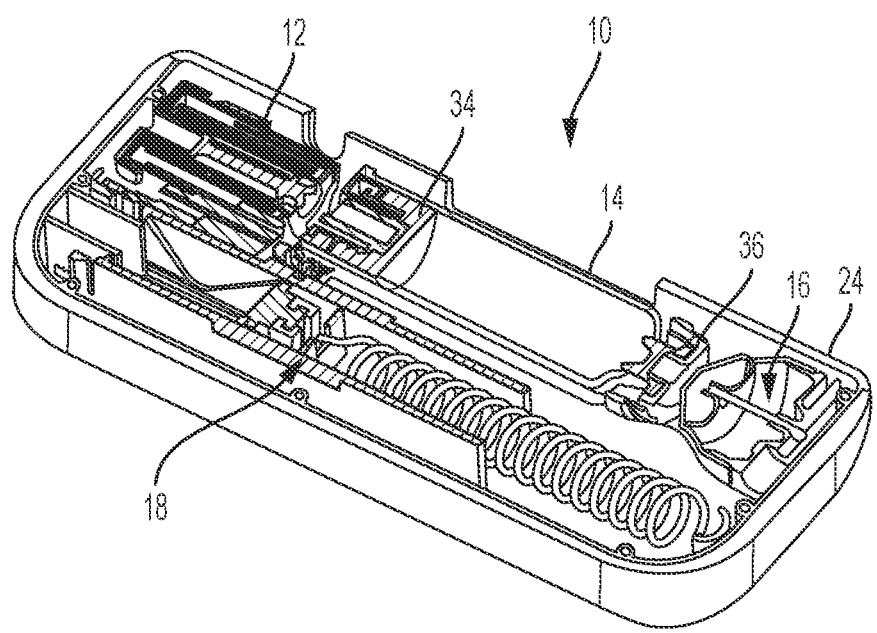
FIG. 2 is a perspective, cross-sectional view of the drug delivery system of FIG. 1 according to one aspect of the present invention.
Figure 3:
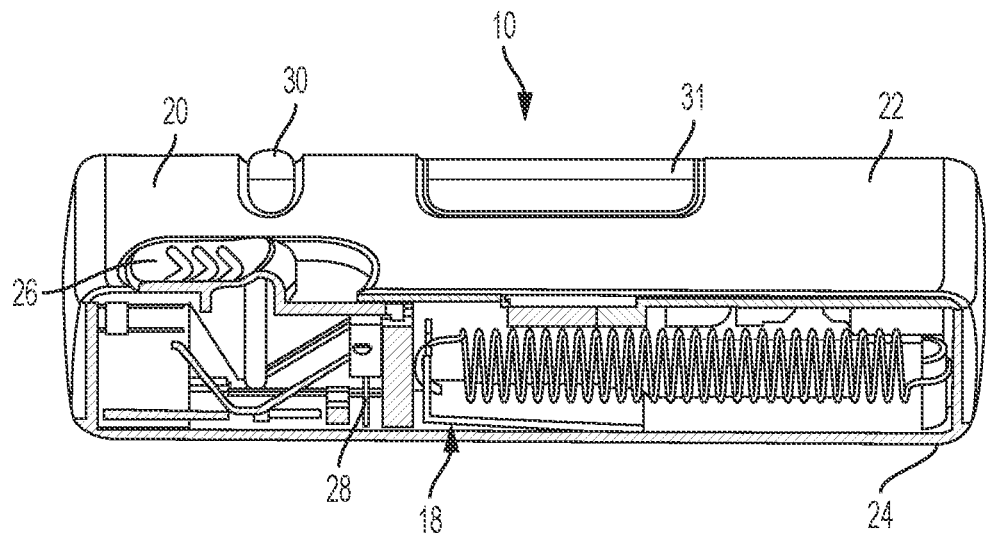
FIG. 3 is a front, cross-sectional view of the drug delivery system of FIG. 1 according to one aspect of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Referring to FIGS. 1-15, a drug delivery system 10 according to one aspect of the present disclosure includes a drive assembly 12, a container 14, a valve assembly 16, and a needle actuator assembly 18. The drive assembly 12, the container 14, the valve assembly 16, and the needle actuator assembly 18 are at least partially positioned within a cavity defined by a housing 20. The housing 20 includes a top portion 22 and a bottom portion 24, although other suitable arrangements for the housing 20 may be utilized. In one aspect, the drug delivery system 10 is an injector device configured to be worn or secured to a user and to deliver a predetermined dose of a medicament provided within the container 14 via injection into the user. The system 10 may be utilized to deliver a "bolus injection" where a medicament is delivered within a set time period. The medicament may be delivered over a time period of up to 45 minutes, although other suitable injection amounts and durations may be utilized. A bolus administration or delivery can be carried out with rate controlling or have no specific rate controlling. The system 10 may deliver the medicament at a fixed pressure to the user with the rate being variable. The general operation of the system 10 is described below in reference to FIGS. 1-15.

Referring again to FIGS. 1-15, the system 10 is configured to operate through the engagement of an actuation button 26 by a user, which results in a needle 28 of the needle assembly 18 piercing the skin of a user, the actuation of the drive assembly 12 to place the needle 28 in fluid communication with the container 14 and to expel fluid or medicament from the container 14, and the withdrawal of the needle 28 after injection of the medicament is complete. The general operation of a drug delivery system is shown and described in International Publication Nos. 2013/155153 and 2014/179774, which are hereby incorporated by reference in their entirety. As set forth in International Patent Application Publication No. 2014/179774, system 10 may include an adhesive for attaching the device to a patient's skin. According to one embodiment, the adhesive is an adhesive pad secured on one side to the housing 20, and having a patient adhesive on the opposing side. A removable adhesive liner preferably protects the patient adhesive, and is removed prior to securing the device to the patient's skin. The housing 20 of the system 10 includes an indicator window 30 for viewing an indicator arrangement 32 configured to provide an indication to a user on the status of the system 10 and a container window 31 for viewing the container 14. The indicator window 30 may be a magnifying lens for providing a clear view of the indicator arrangement 32. The indicator arrangement 32 moves along with the needle actuator assembly 18 during use of the system 10 to indicate a pre-use status, use status, and post-use status of the system 10. The indicator arrangement 32 provides visual indicia regarding the status, although other suitable indicia, such an auditory or tactile, may be provided as an alternative or additional indicia.

Figure 4:
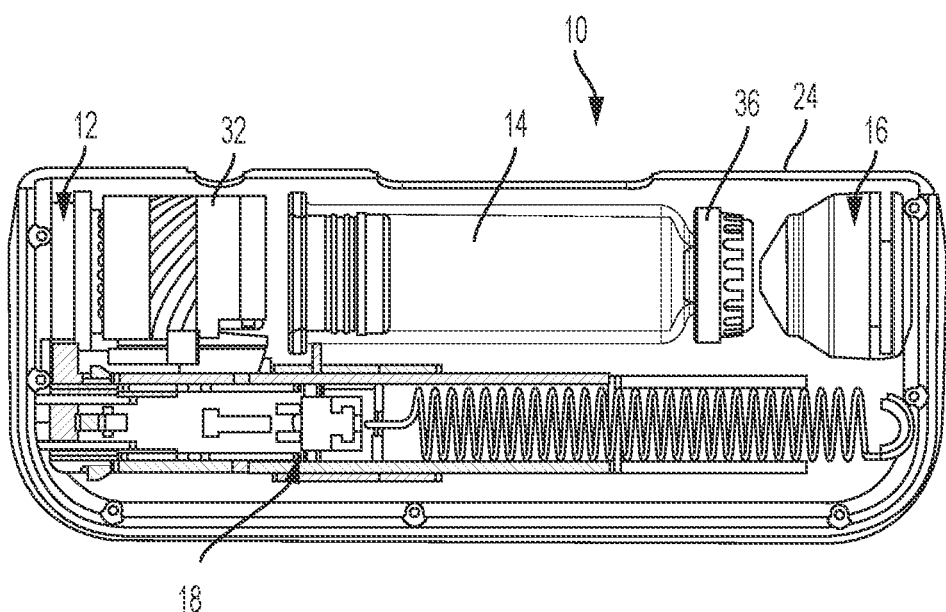
FIG. 4 is a top view of the drug delivery system of FIG. 1 according to one aspect of the present invention, showing a top portion of the housing removed and the drug delivery system in a pre-use position.
Figure 5:
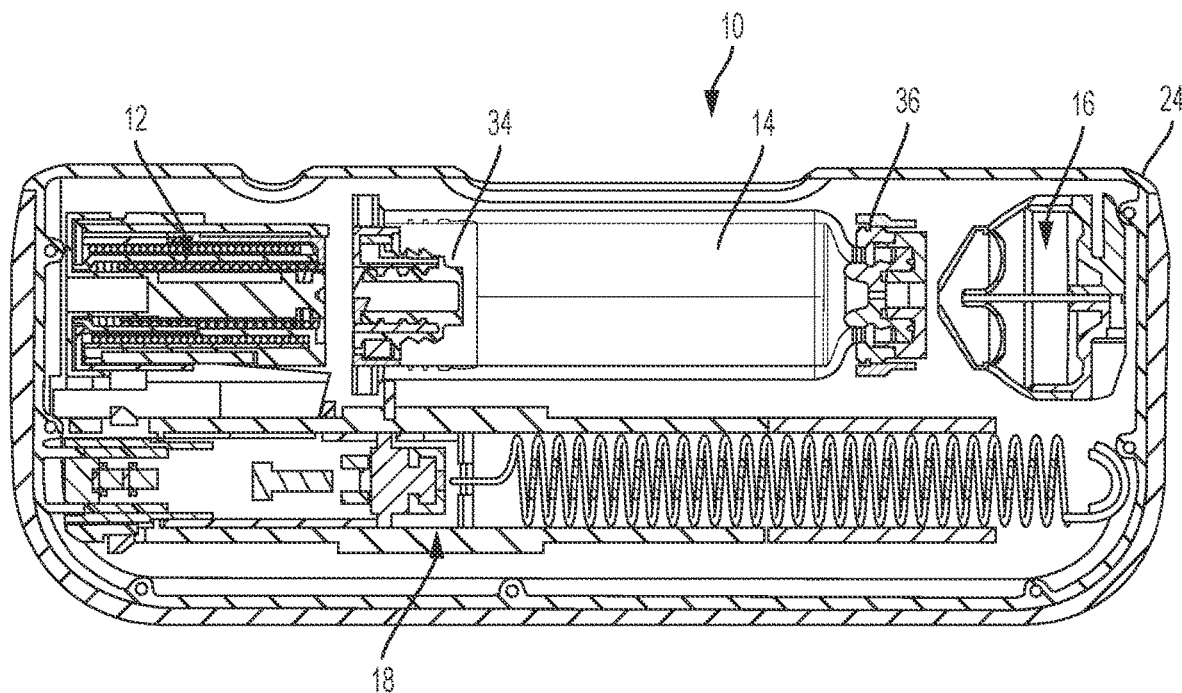
FIG. 5 is a top, cross-sectional view of the drug delivery system of FIG. 1 according to one aspect of the present invention, showing the drug delivery system in a pre-use position.
Figure 6:
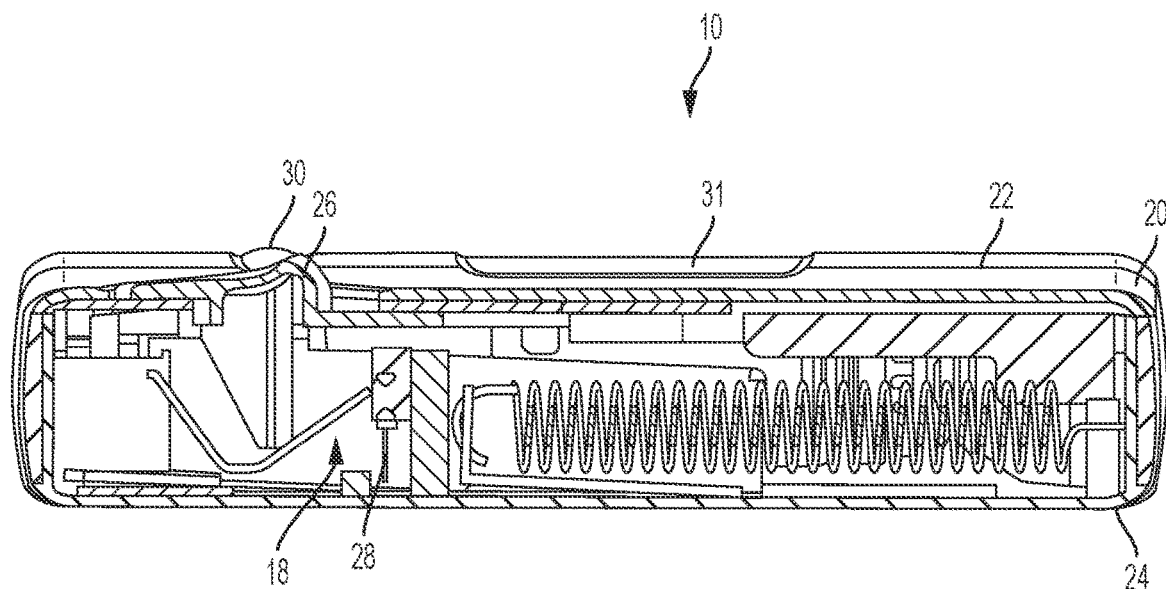
FIG. 6 is a front, cross-sectional view of the drug delivery system of FIG. 1 according to one aspect of the present invention, showing the drug delivery system in a pre-use position.
Figure 7:
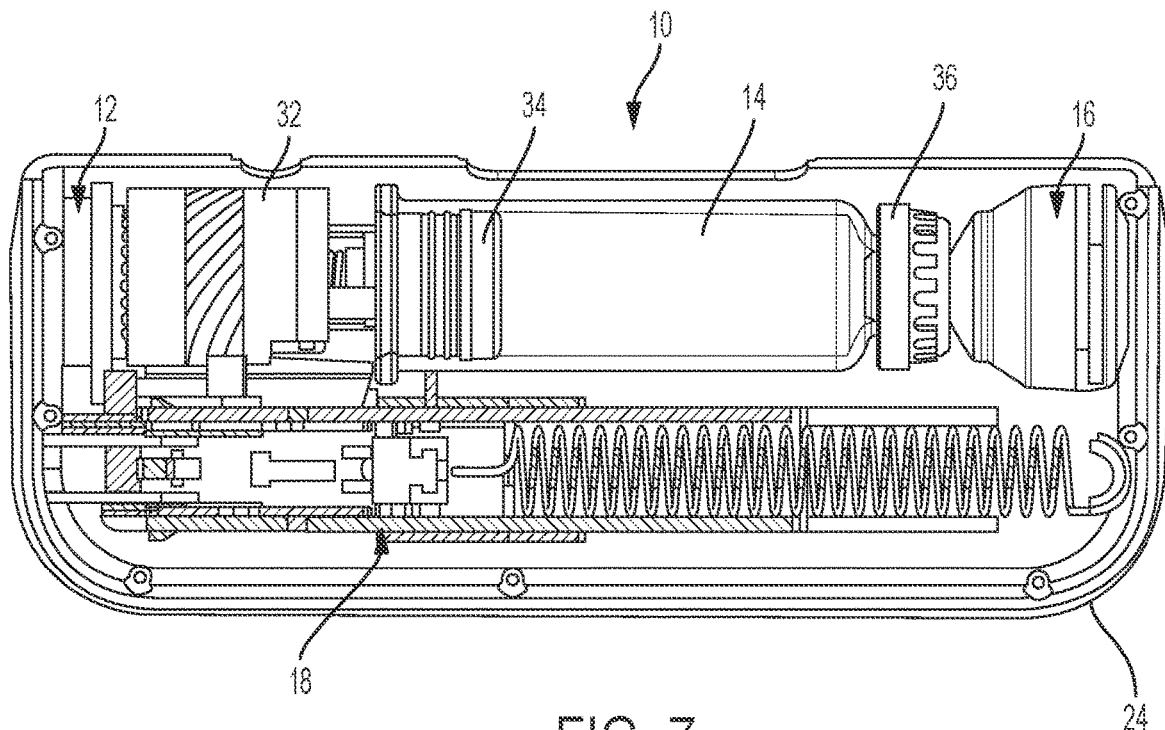
FIG. 7 is a top view of the drug delivery system of FIG. 1 according to one aspect of the present invention, showing a top portion of the housing removed and the drug delivery system in an initial actuation position.
Figure 8:
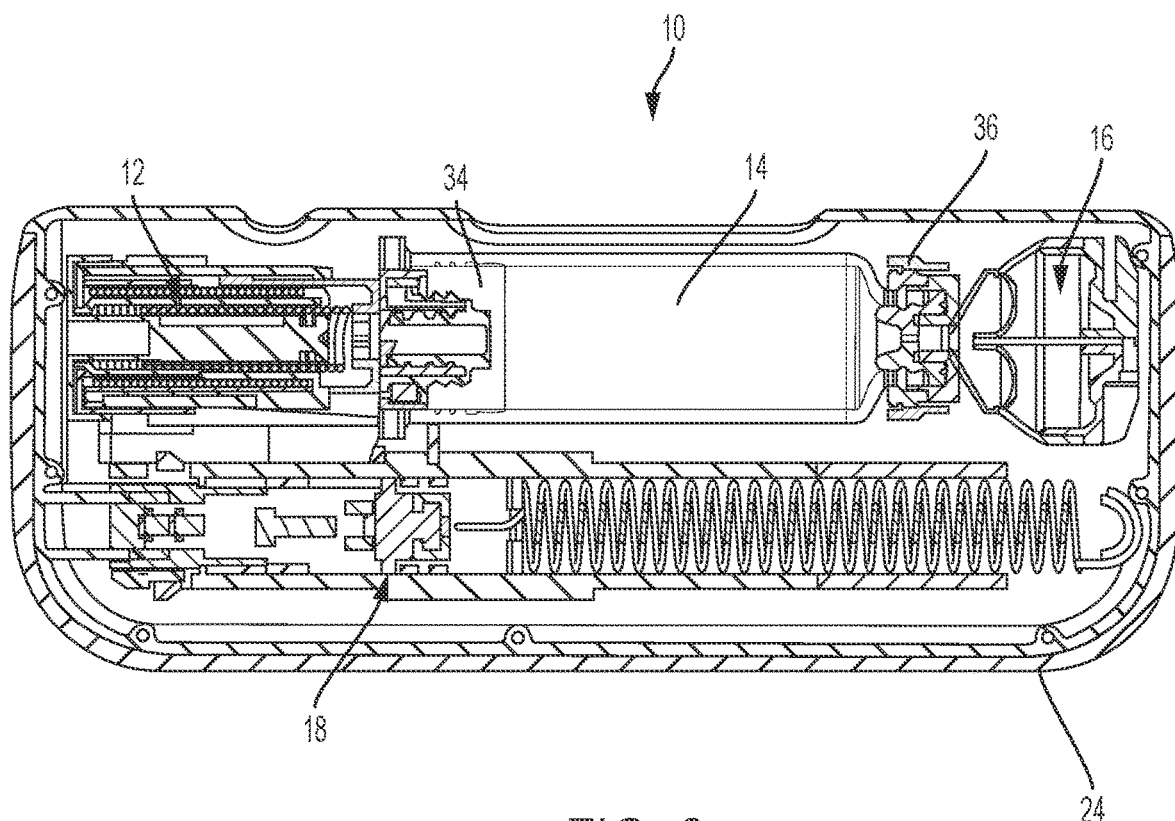
FIG. 8 is a top, cross-sectional view of the drug delivery system of FIG. 1 according to one aspect of the present invention, showing the drug delivery system in an initial actuation position.
Figure 9:
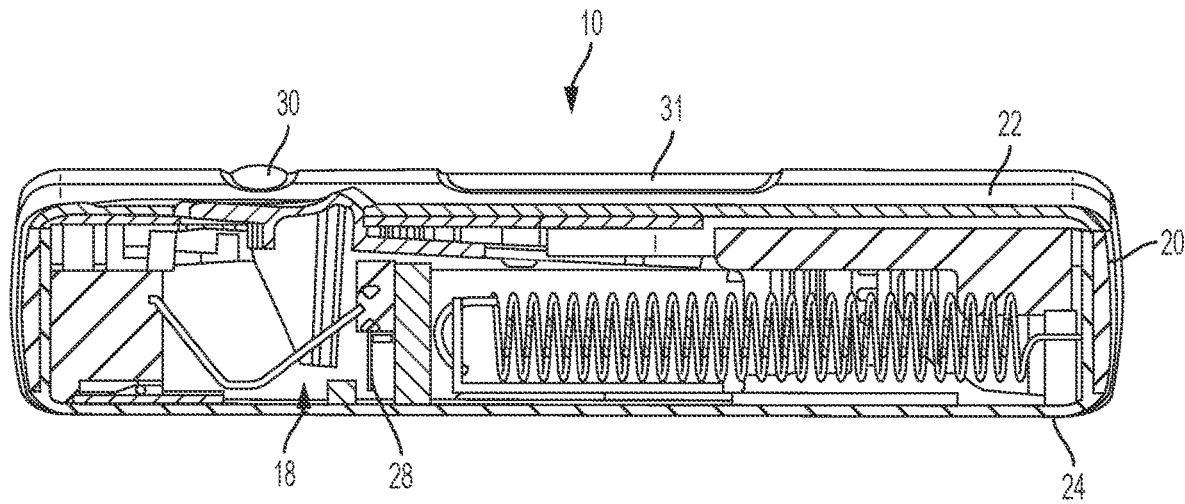
FIG. 9 is a front, cross-sectional view of the drug delivery system of FIG. 1 according to one aspect of the present invention, showing the drug delivery system in an initial actuation position.

Referring to FIGS. 4-6, during a pre-use position of the system 10, the container 14 is spaced from the drive assembly 12 and the valve assembly 16 and the needle 28 is in a retracted position. During the initial actuation of the system 10, as shown in FIGS. 7-9, the drive assembly 12 engages the container 14 to move the container 14 toward the valve assembly 16, which is configured to pierce a closure 36 of the container 14 and place the medicament within the container 14 in fluid communication with the needle 28 via a tube (not shown) or other suitable arrangement. The drive assembly 12 is configured to engage a stopper 34 of the container 14, which will initially move the entire container 14 into engagement with the valve assembly 16 due to the incompressibility of the fluid or medicament within the container 14. The initial actuation of the system 10 is caused by engagement of the actuation button 26 by a user, which releases the needle actuator assembly 18 and the drive assembly 12 as discussed below in more detail. During the initial actuation, the needle 28 is still in the retracted position and about to move to the extended position to inject the user of the system 10.

Figure 10:
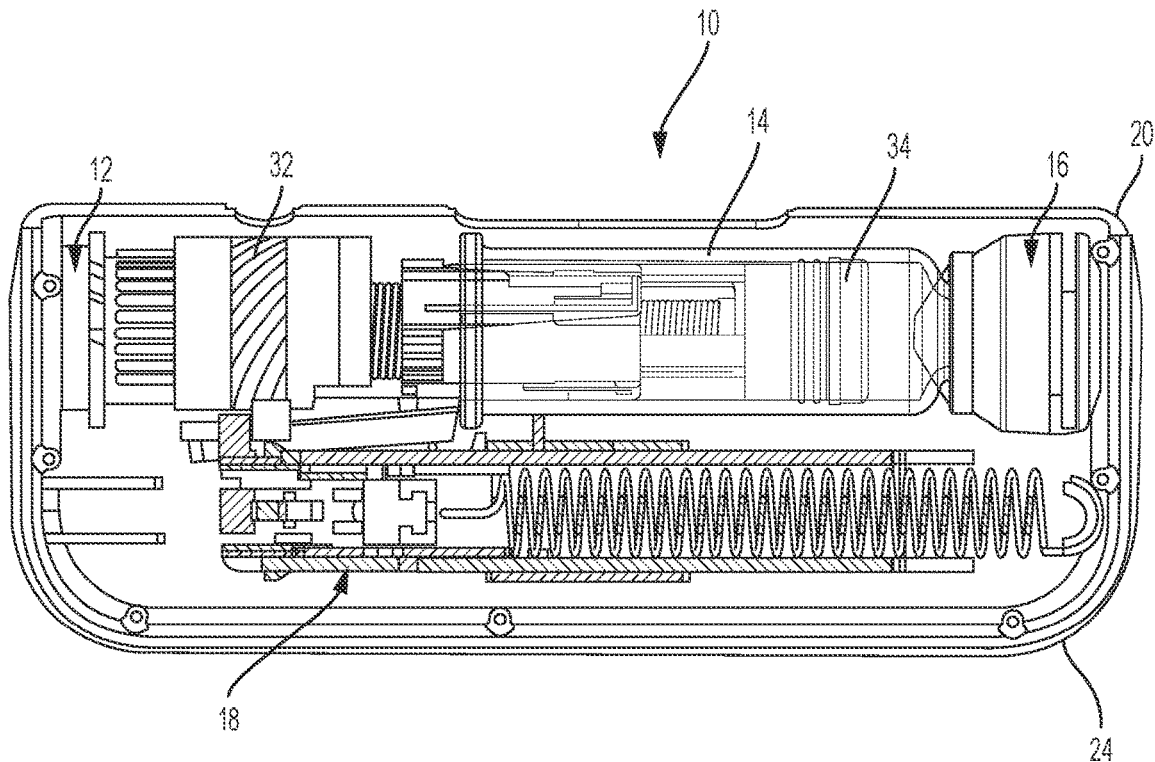
FIG. 10 is a top view of the drug delivery system of FIG. 1 according to one aspect of the present invention, showing a top portion of the housing removed and the drug delivery system in a use position.
Figure 11:
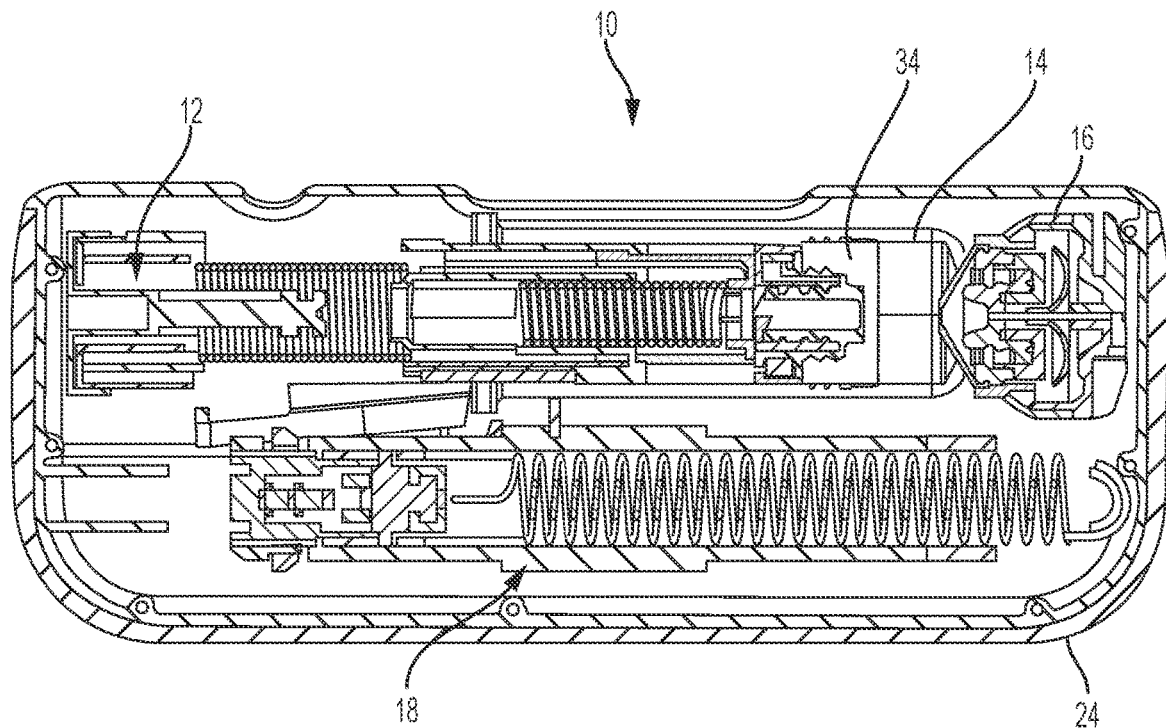
FIG. 11 is a top, cross-sectional view of the drug delivery system of FIG. 1 according to one aspect of the present invention, showing the drug delivery system in a use position.
Figure 12:
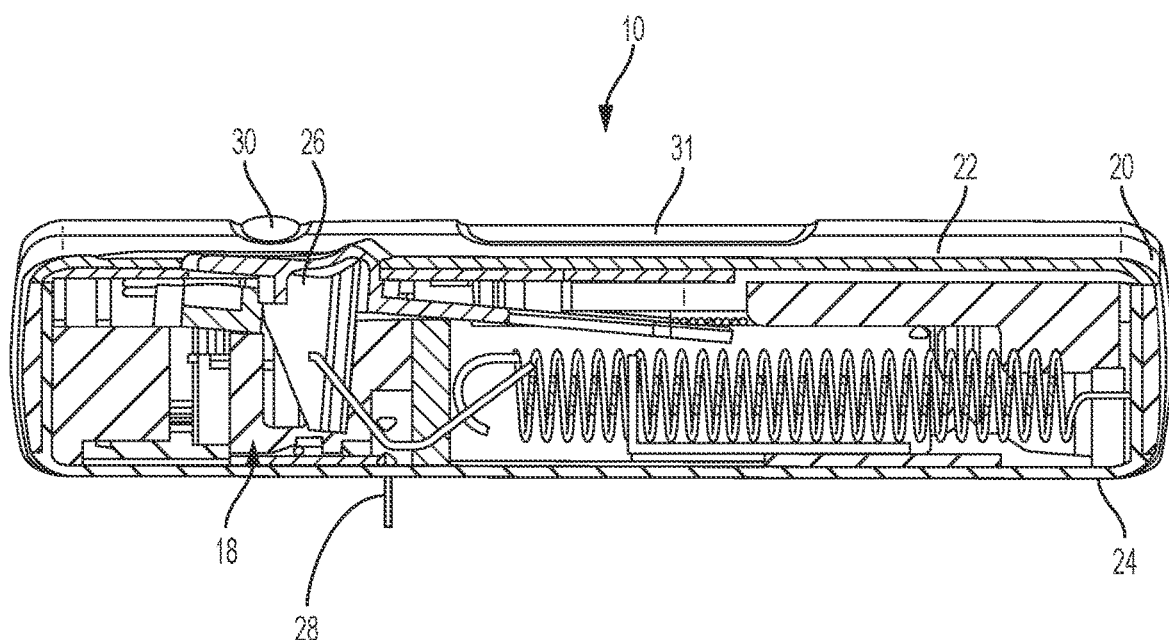
FIG. 12 is a front, cross-sectional view of the drug delivery system of FIG. 1 according to one aspect of the present invention, showing the drug delivery system in a use position.
Figure 13:
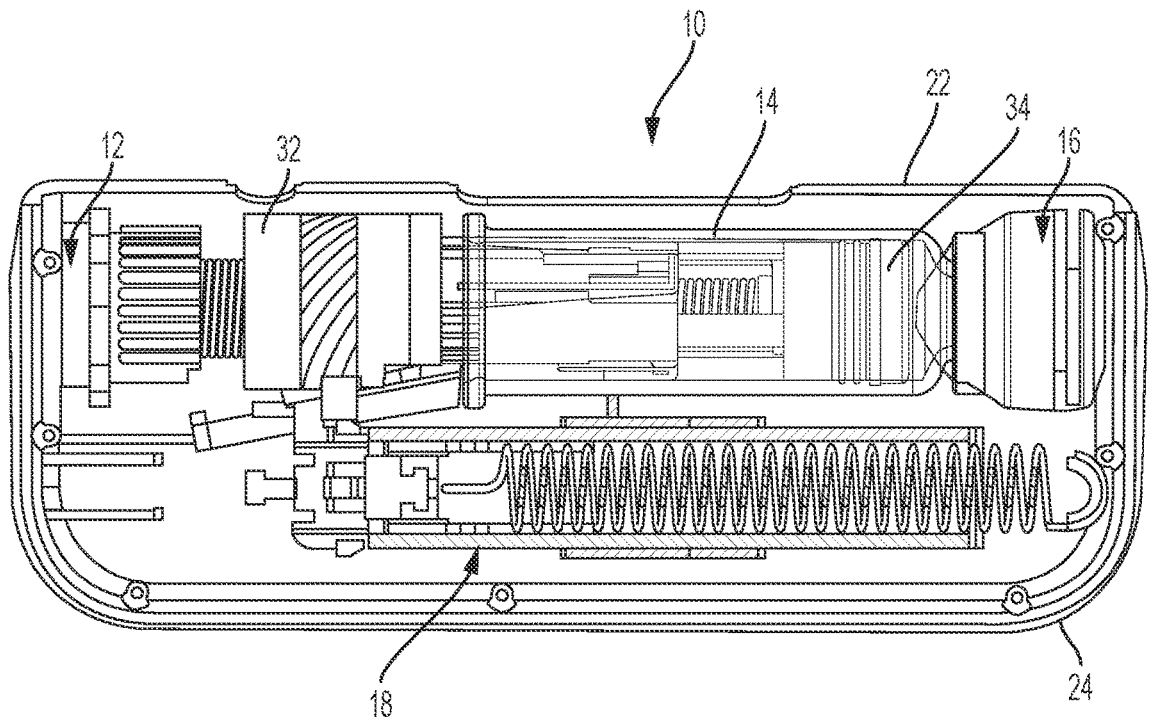
FIG. 13 is a top view of the drug delivery system of FIG. 1 according to one aspect of the present invention, showing a top portion of the housing removed and the drug delivery system in a post-use position.
Figure 14:
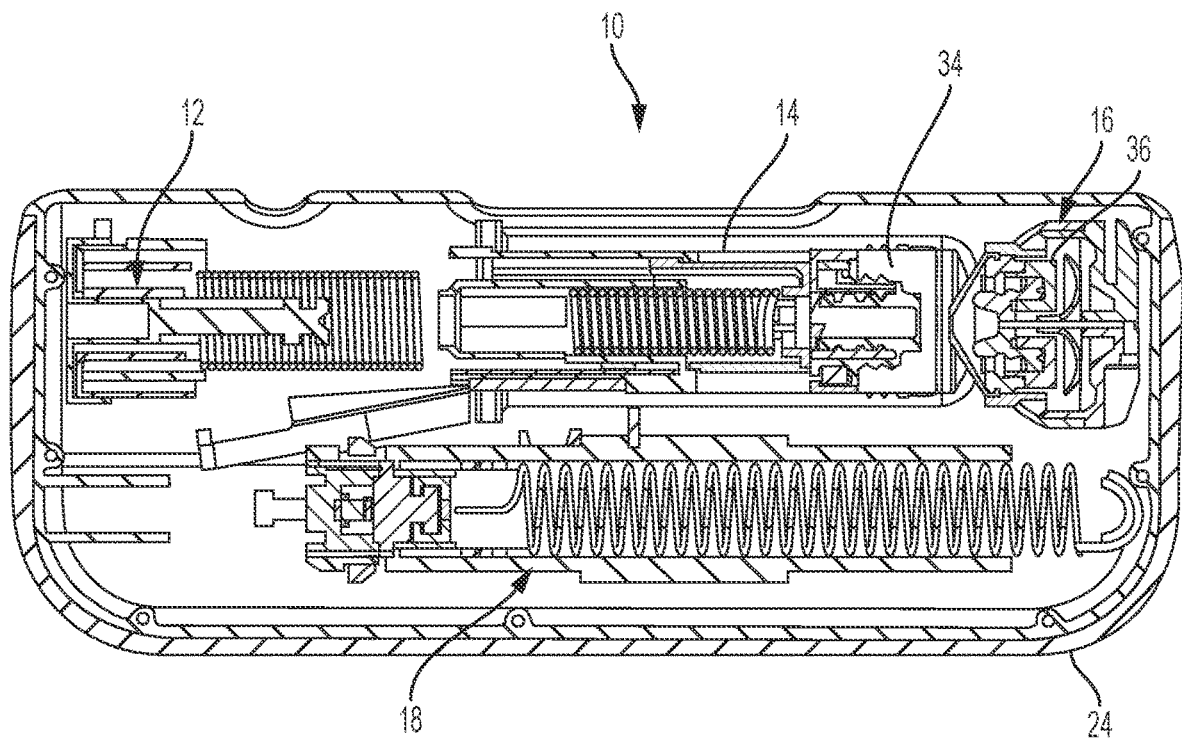
FIG. 14 is a top, cross-sectional view of the drug delivery system of FIG. 1 according to one aspect of the present invention, showing the drug delivery system in a post-use position.
Figure 15:
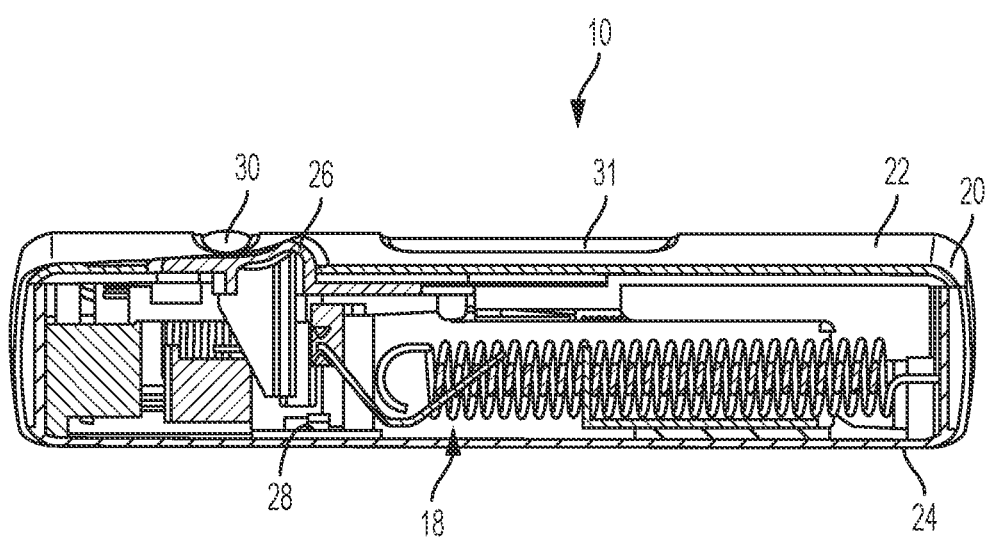
FIG. 15 is a front, cross-sectional view of the drug delivery system of FIG. 1 according to one aspect of the present invention, showing the drug delivery system in a post-use position.

During the use position of the system 10, as shown in FIGS. 10-12, the needle 28 is in the extended position at least partially outside of the housing 20 with the drive assembly 12 moving the stopper 34 within the container 14 to deliver the medicament from the container 14, through the needle 28, and to the user. In the use position, the valve assembly 16 has already pierced a closure 36 of the container 14 to place the container 14 in fluid communication with the needle 28, which also allows the drive assembly 12 to move the stopper 34 relative to the container 14 since fluid is able to be dispensed from the container 14. At the post-use position of the system 10, shown in FIGS. 13-15, the needle 28 is in the retracted position and engaged with a pad to seal the needle 28 and prevent any residual flow of fluid or medicament from the container 14. The container 14 and valve assembly 16 may be the container 14 and valve assembly 16 shown and described in International Publication No. WO 2015/081337, which is hereby incorporated by reference in its entirety.

Figure 16:
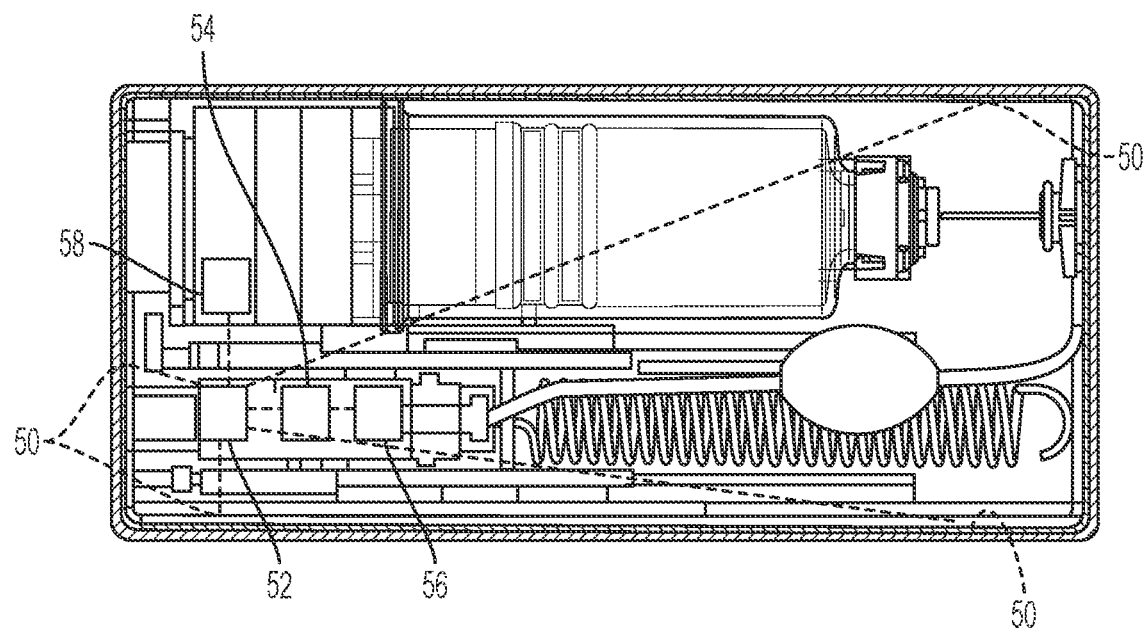
FIG. 16 is a top view of a drug delivery system including a sterilization arrangement according to another aspect of the present invention, showing a top portion of the housing removed.
Figure 17:
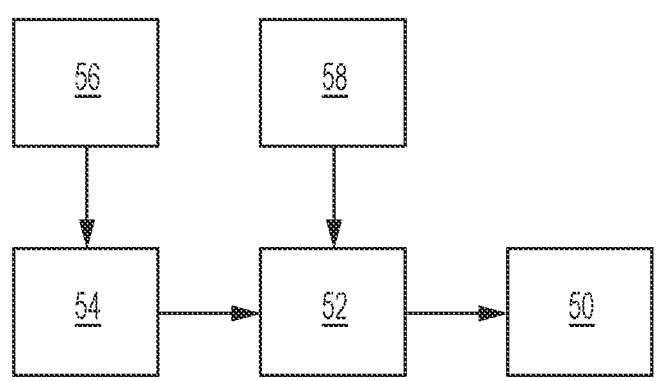
FIG. 17 is a schematic illustration of the sterilization arrangement of the drug delivery system of FIG. 16.

Referring to FIGS. 16 and 17, in one aspect, a sterilizer is also provided in the system 10. The sterilizer includes a light source 50 to sterilize the inner components of the system 10. In one aspect, the light source 50 provides ultraviolet (UV) light to the inner cavity of the housing 20. The UV light provided by the light source 50 is directed to the inner components of the system 10 to sterilize the inner components, such as the drive assembly 12, the container 14, the valve assembly 16, and the needle actuator assembly 18. In one aspect, the light source 50 includes one or more light emitting diode (LED) lights. In one aspect, a single light source 50 is provided in the housing 20. It is also contemplated that a plurality of light sources 50 are provided in the housing 20. In one aspect, four light sources 50 are provided in the housing 20. In one aspect, the light source 50 shines UV light on each component in the system 10. In another aspect, the light source 50 shines UV light on a portion of the components in the system 10. Any bacteria or contaminants growing or developing inside of the system 10 are sterilized by the UV light to provide a sterile environment inside the housing 20. In one aspect, the light sources 50 are each positioned on a different inner side surface of the housing 20.

Referring again to FIGS. 16 and 17, in one aspect, the light sources 50 are connected to a power source 52. The power source 52 may be any arrangement capable of providing power to illuminate the light sources 50. The power source 52 may be provided within the housing 20. In particular, the power source 52 may be provided on the top portion 22 and/or the bottom portion 24. In one aspect, the power source 52 includes at least one battery. It is also contemplated that the power source 52 may be provided as a power source external to the housing 20. For example, the power source 52 may be a battery pack wired to the housing 20, but provided external to the housing 20. The power source 52 may be replaceable and/or rechargeable. In one aspect, a plurality of batteries are provided as the power source 52 to power the light sources 50. The batteries may be charged by an external connector, such as a cord extending to an electrical outlet, or by an induction arrangement (not shown).

Referring again to FIGS. 16 and 17, a sensor 54 is also provided in the housing 20 to actuate the light sources 50 upon initiation of the drug delivery actuation process. The sensor 54 is configured to sense when the drug delivery actuation process has been initiated and sends a signal to the power source 52 to supply power from the power source 52 to the light sources 50 so that UV light is emitted by the light sources 50 to sterilize one or more components in the system 10. In one aspect, the sensor 54 is a Hall Effect transistor sensor that cooperates with a magnet 56 provided on or in a switch or button of the system 10. In one aspect, the sensor 54 is provided on the actuation button 26 of the system 10. It is also contemplated that the sensor 54 could be provided on a switch or button (not shown) separate from the actuation button 26 so that the light source 50 could be activated independently of the drug delivery actuation process. When the actuation button 26 of the system 10 is actuated, the sensor 54 sends a signal to activate the power source 52 to supply power to the light sources 50. Therefore, as the system 10 proceeds through the drug delivery process, the light sources 50 sterilize the inner components of the system 10. In another aspect, a timer 58 is connected to the power source 52 so that, after a predetermined amount of time of activation, the light sources 50 will be turned off. The length of time that the light sources 50 are activated is adjustable by the timer 58.

Referring to the device of FIG. 16 and the logic diagram of FIG. 17, a method of sterilizing a drug delivery system 10 is described. As described above, to actuate the drug delivery process, the actuation button 26 is depressed. As the actuation button 26 is depressed, the magnet 56 provided in the actuation button 26 actuates the sensor 54. The sensor 54 sends a signal to the power source 52 to activate the power source 52. The power source 52 then supplies power to the light sources 50 to activate the LED lights within the light sources 50. The LED lights of the light sources 50 cast UV light over the inner components of the system 10 to sterilize the inner components. In one aspect, the UV light is cast on at least one of the drive assembly 12, the container 14, the valve assembly 16, and the needle actuator assembly 18. It is also contemplated that the UV light may be cast on each of the drive assembly 12, the container 14, the valve assembly 16, and the needle actuator assembly 18. With the actuation button 26 having been depressed and the light sources 50 having been activated, after a predetermined amount of time, the timer 58 shuts off the light sources 50 to stop the emittance of the UV light. After use of the system 10, a user can recharge the power source 54 either internally or externally of the housing 20.

Elements of one disclosed aspect can be combined with elements of one or more other disclosed aspects to form different combinations, all of which are considered to be within the scope of the present invention.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A wearable drug delivery system comprising:
a housing defining a cavity, the housing comprising a window configured to allow a patient to view a portion of the cavity;
a medicament container configured to be received within the cavity and to receive a medicament;
a first needle configured to be placed in fluid communication with the medicament container, the first needle having a first position spaced from the medicament container, and a second position in which at least a portion of the first needle is received within the medicament container;
a second needle configured to pierce a patient's skin, and to deliver the medicament to the patient, the second needle in fluid communication with the first needle;
an adhesive coupled to the housing and configured to releasably couple the wearable drug delivery system to the patient's skin;
a button to initiate a drug delivery process;
an ultraviolet (UV) light source fixed within the cavity and configured to sterilize a portion of one or more surfaces received within the cavity of the housing of the wearable drug delivery system following initiation of the drug delivery process;
a power source operatively connected to the UV light source;
a timer operatively connected to the UV light source and configured to shut off the UV light source after a predetermined amount of time; and
an indicator configured to convey a status of the drug delivery process.

2. The wearable drug delivery system of claim 1, wherein the window is configured to allow a patient to view a portion of the medicament container.

3. The wearable drug delivery system of claim 1, wherein the UV light source comprises a light emitting diode (LED) that is configured to emit UV light to sterilize the portion of the one or more surfaces received within the cavity of the housing of the wearable drug delivery system.

4. The wearable drug delivery system of claim 3, wherein the LED is configured to sterilize a portion of the container.

5. The wearable drug delivery system of claim 3, wherein the LED is configured to sterilize a portion of the first needle.

6. The wearable drug delivery system of claim 3, wherein the UV light source comprises a plurality of LEDs.

7. The wearable drug delivery system of claim 3, further comprising a sensor configured to detect when the button has initiated the drug delivery process and to cause the power source to supply power to the LED.

8. The wearable drug delivery system of claim 1, wherein the indicator comprises an auditory, a tactile, or a visual indicator.

9. The wearable drug delivery system of claim 8, wherein the indicator is a visual indicator.

10. The wearable drug delivery system of claim 9, wherein the visual indicator is arranged within the housing and is visible through the window.

11. The wearable drug delivery system of claim 8, wherein the indicator is configured to indicate a pre-use status, a use status, and a post-use status.

12. The wearable drug delivery system of claim 1, wherein the second needle is moveable between an extended position and a retracted position.

13. The wearable drug delivery system of claim 1, wherein the adhesive is an adhesive pad.

14. The wearable drug delivery system of claim 1, further comprising a drive assembly received within the cavity and configured to cause medicament to be expelled from the contained.

15. The wearable drug delivery system of claim 14, wherein the drive assembly is configured to deliver medicament to the patient at a fixed pressure.

16. The wearable drug delivery system of claim 14, wherein the drive assembly is configured to deliver medicament to the patient at a controlled rate.

17. The wearable drug delivery system of claim 14, wherein the UV light source comprises a LED that is configured to emit UV light to sterilize a portion of the drive assembly.

* * * * *